US011229571B2

(12) United States Patent
Truchi et al.

(10) Patent No.: US 11,229,571 B2
(45) Date of Patent: Jan. 25, 2022

(54) GRIPPING DEVICE FOR A URINAL BAG

(71) Applicant: CLEANIS, Arcueil (FR)

(72) Inventors: Guillaume Truchi, Marseilles (FR); Sophia Idris Hadji, Paris (FR)

(73) Assignee: CLEANIS, Arcueil (FR)

( * ) Notice: Subject to any disclaimer, the term of this patent is extended or adjusted under 35 U.S.C. 154(b) by 0 days.

(21) Appl. No.: 17/047,439

(22) PCT Filed: Apr. 24, 2019

(86) PCT No.: PCT/EP2019/060432
§ 371 (c)(1),
(2) Date: Oct. 14, 2020

(87) PCT Pub. No.: WO2019/206941
PCT Pub. Date: Oct. 31, 2019

(65) Prior Publication Data
US 2021/0145681 A1 May 20, 2021

(30) Foreign Application Priority Data

Apr. 27, 2018 (FR) ...................................... 1853736

(51) Int. Cl.
*A61G 9/00* (2006.01)
(52) U.S. Cl.
CPC .................................. *A61G 9/006* (2013.01)
(58) Field of Classification Search
CPC ...................................................... A61G 9/006
USPC .......................................................... 4/144.2
See application file for complete search history.

(56) References Cited

U.S. PATENT DOCUMENTS

| 3,597,770 | A | * | 8/1971 | Jacuzzi | A61G 9/006 4/144.2 |
| 4,149,745 | A | * | 4/1979 | Willis | E01H 1/1206 15/257.1 |
| 4,305,161 | A | | 12/1981 | Diaz | |
| 4,707,864 | A | * | 11/1987 | Ikematsu | A61F 5/455 4/144.3 |
| 5,009,236 | A | | 4/1991 | Brothers | |
| 5,457,823 | A | * | 10/1995 | Mojena | A47K 11/12 4/144.2 |
| 5,571,095 | A | | 11/1996 | Lu | |
| 2004/0195467 | A1 | * | 10/2004 | Passage | B65F 1/1415 248/99 |
| 2007/0031068 | A1 | | 2/2007 | Gillis | |
| 2010/0305525 | A1 | | 12/2010 | Tanguay | |

FOREIGN PATENT DOCUMENTS

| EP | 0 150 027 A2 | 7/1985 |
| GB | 1 422 638 A | 1/1976 |
| WO | 2009/146534 A1 | 12/2009 |

OTHER PUBLICATIONS

Jun. 4, 2019 Search Report issued in International Patent Application No. PCT/EP2019/060432.

* cited by examiner

*Primary Examiner* — Huyen D Le
(74) *Attorney, Agent, or Firm* — Oliff PLC

(57) ABSTRACT

A holder device including a urinal bag support and a handle fixed to the support, wherein the support includes first and second spacers for holding a urinal bag in first and second open positions, respectively, in which positions the bag opens in first and second different orientations, respectively.

22 Claims, 2 Drawing Sheets

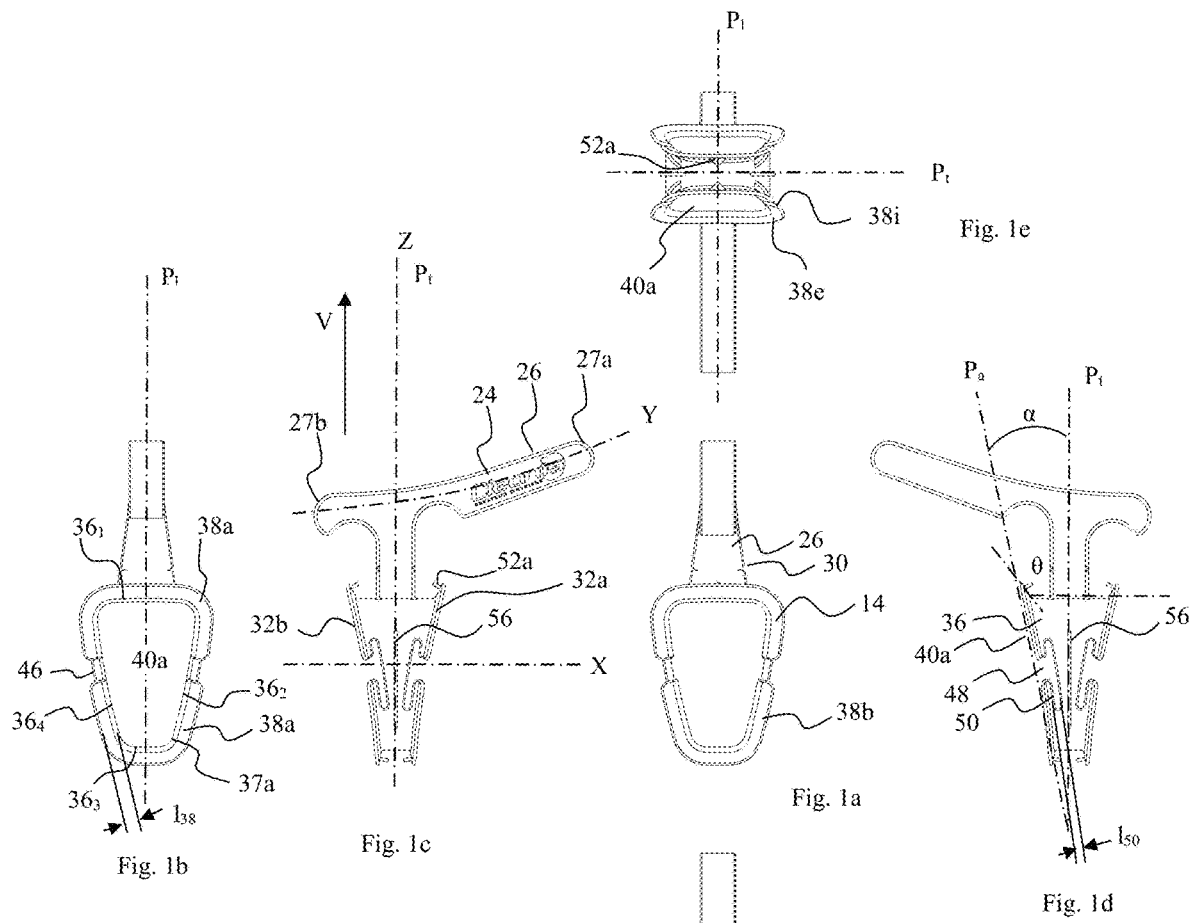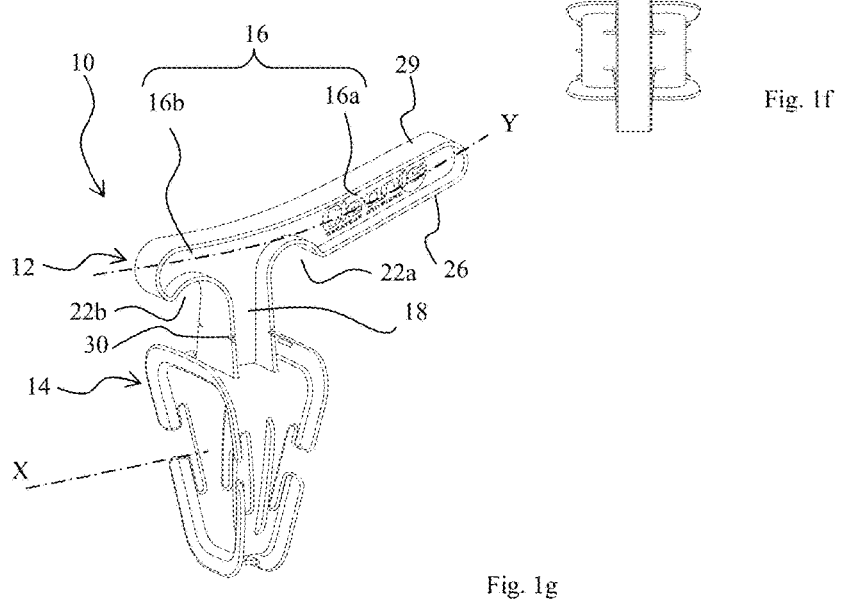

GRIPPING DEVICE FOR A URINAL BAG

TECHNICAL FIELD

The invention relates to a holder device intended to hold a urinal bag in the open position and intended for handling this bag. The invention also relates to a urinal device comprising a holder device according to the invention, to which a urinal bag is fixed. The invention finally relates to a method for packaging the urinal bag after use.

PRIOR ART

In hospitals, certain patients are unable to use the toilet for urinating. Conventionally, these patients therefore urinate into a fluid tight urinal bag which they fix beforehand, in an open position, to a holder device that is easy to handle. Such a holder device is described for example in US 2010/0305525 and may comprise:
- a urinal bag support designed to hold the urinal bag in the open position; and
- a handle, fixed to the support.

After the patient has urinated into the bag, the support can be hung from the bars of the bed while awaiting collection by a caregiver. The caregiver then detaches the bag from the support, then disposes of it. The holder device is then ready to receive a new urinal bag.

The holder device needs to be as multifunctional as possible in order to suit patients of different builds.

Its environmental impact needs to be as low as possible. In particular, the quantity of material used in its manufacture and the amount of waste produced need to be minimized.

The holder device also needs to be as low in bulk as possible so that it can be stored efficiently, in order to limit storage space in hospitals.

Finally, the method used to manufacture the holder device needs to be as simple and quick as possible.

There is an ongoing need to meet these requirements as well as possible.

It is an object of the invention to, at least partially, meet this need.

SUMMARY OF THE INVENTION

The invention proposes a holder device comprising a urinal bag support and a handle fixed to the support, preferably formed integrally with the support. Notably, the support comprises first and second spacers configured to keep the urinal bag in first and second open positions respectively, in which first and second open positions the bag opens in first and second different orientations respectively.

As will be seen in greater detail in the remainder of the description, the possibility of orienting the urinal bag in various ways makes the holder device very multifunctional.

A holder device according to the invention may also comprise one or more of the following optional features:
- the first and second orientations are opposite and preferably colinear;
- the holder device comprises a hook designed to allow said bag to be constricted while said bag is fixed to any one of the first and second spacers, so as to isolate an interior volume of said bag from the exterior environment;
- the holder device comprises a slot for affixing, by forceable insertion, a closure tie for closing said bag;
- at least one of the first and second spacers defines a bearing flange configured so that, in service, it bears against the skin of a patient, said bearing flange preferably being substantially flat, and having a width greater than 0.5 cm, preferably greater than 0.8 cm and/or less than 2 cm, preferably less than 1.5 cm, the bearing flange preferably being interrupted by at least one interruption zone, preferably by two interruption zones;
- as a preference, the first and second spacers define first and second bearing flanges intended respectively, in service, to bear against the skin of a patient, at least, preferably each, bearing flange exhibiting a width greater than 0.5 cm, preferably greater than 0.8 cm and/or less than 2 cm, preferably less than 1.5 cm, preferably being substantially flat, and preferably being interrupted by at least one interruption zone, preferably by two interruption zones;
- one, preferably each, bearing flange defines an opening which extends in an overall plane which, with a transverse median plane of the support, makes an angle greater than 10° and less than 30;
- the holder device comprises an attaching lug projecting from the bearing flange over a height greater than 1 mm and less than 8 mm;
- the support comprises a sleeve provided, at each of its two ends, with one said bearing flange, the support preferably being symmetrical with respect to a transverse median plane;
- the sleeve is cylindrical, preferably with a trapezoidal transverse section, the trapezoidal transverse section pointing in the opposite direction to the handle;
- as a preference, each bearing flange extends radially (with reference to the axis of the sleeve) outward from the sleeve, preferably at one end of the respective sleeve;
- the handle defines at least one indentation configured to allow the holder device to be hung stably from a horizontal bar exhibiting a diameter greater than 1 cm;
- the handle comprises a stick and a crosspiece rigidly connecting the stick to the support, the crosspiece being designed to space the stick away from the first and/or second spacer, preferably from the first and the second spacer,
- the crosspiece is configured to space the stick radially away from the axes of the first and second openings defined by the first and second spacers respectively;
- the axis of the crosspiece preferably forming, with the axes of the openings defined by the first and second spacers, an angle greater than 60°, 70°, 80° and/or less than 120°, 110°, 100°, preferably of around 90°, the axis of the crosspiece preferably being coplanar with the axes of said openings;
- the minimum distance between the stick and the support is preferably greater than 2 cm, greater than 3 cm or greater than 4 cm;
- as a preference, the crosspiece is substantially perpendicular to the surface of the support and/or of the stick;
- the crosspiece is preferably substantially perpendicular to the axis of said sleeve;
- as a preference, the crosspiece exhibits a length greater than 2 cm, greater than 3 cm or greater than 4 cm;
- the handle comprises a stick made up of a proximal part and a distal part, and a crosspiece rigidly connecting the stick to the support and connected to the juncture between the proximal and distal parts of the stick, said indentations being created in the corners formed by the crosspiece on the one hand, and by the proximal and distal parts of the stick, respectively;

the stick extends in an overall direction that forms, with a plane perpendicular to the crosspiece, an angle greater than 10°;

the handle is made up of a web edged with a peripheral flange exhibiting a minimum width greater than 0.5 cm;

the first and second bearing flanges are configured to keep the urinal bag elastically in the first and second open positions respectively.

The invention also relates to a urinal device comprising a holder device according to the invention and a urinal bag designed to be fixed to the first or the second spacer in the first and second open positions respectively.

The invention finally relates to a method for packaging a urinal bag initially fixed removably to a spacer of a holder device and held in the open position by said spacer. Notably, the method comprises, after use of the urinal bag, a step wherein the bag is constricted in a notch of the holder device, namely inserted into the notch so as to isolate the inside of the bag from the exterior environment.

As will be seen in greater detail in the remainder of the description, this method makes it possible, after use, to quickly and effectively isolate the urine contained inside the bag, thereby preventing the spread of unpleasant odors, and promoting hygiene.

The holder device is preferably a holder device according to the invention.

The method according to the invention may further comprise one or more of the following optional features:

prior to being inserted in the notch, the part of the bag that is to be inserted into the notch is preferably twisted on itself preferably over more than one turn, preferably more than 2 turns;

on insertion into the notch, the urinal bag remains held in the open position by said spacer;

after being inserted in the notch, the holder device is hung from a bar of a bed.

Definitions

The adjectives "upper" and "lower" refer to the vertical direction illustrated, in FIG. 1c or 3b, by the arrow V pointing upward.

"Include", "comprise" and "exhibit" are to be interpreted in the broad and nonlimiting sense, unless other indicated.

An angle between two axes is defined by the angle between two planes perpendicular to these axes.

BRIEF DESCRIPTION OF THE FIGURES

Further features and advantages of the invention will become further apparent from reading the detailed description of a preferred embodiment which follows, and from studying the drawing in which:

FIGS. 1a to 1g (collectively referred to as "FIG. 1") depict a holder device viewed from the front, from behind, from the right, from the left, from beneath, from above and in perspective, respectively, in one preferred embodiment of the invention;

FIG. 4a is a perspective illustration of the packaging of the urinal bag depicted in FIG. 2a.

DETAILED DESCRIPTION

Device

Figure 2B:
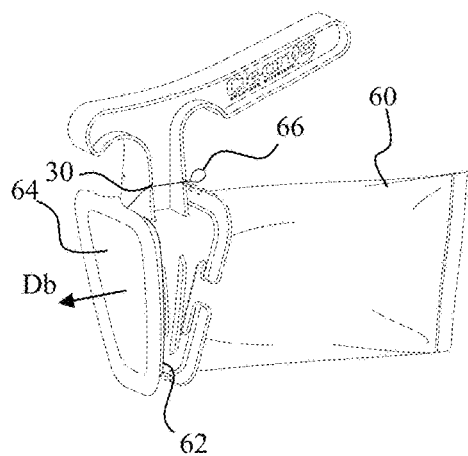
FIGS. 2a and 2b illustrate first and second open positions, respectively, with the holder device of FIG. 1.

FIG. 1 depicts one example of a holder device 10 according to the invention. The adjectives "proximal" and "distal" which are used to describe this example may correspond to the adjectives "first" and "second" used previously and in the claims. They have been used for the sake of clarity.

This holder device comprises a handle 12 exhibiting the overall shape of an asymmetric T, and a substantially tubular support 14 of axis X.

The holder device 10 is preferably one-piece, the support 14 being formed integrally with the handle 12. The device may in particular be manufactured by molding. It therefore has no fixing member joining together the handle 12 and the support 14, and this advantageously makes manufacturing easier.

The handle 12 comprises a stick 16, of axis Y, which defines that part of the handle which is intended to be grasped by the operator. The stick is made up of proximal part 16a and a distal part 16b, and a crosspiece 18, of axis Z, rigidly connecting the stick 16 to the support 14 and connected to the junction between the proximal 16a and distal 16b parts of the stick 16.

As a preference, the overall direction of the stick forms, with a horizontal plane, an angle greater than 10°, preferably greater than 20° and/or less than 50°, preferably less than 40°, an inclination of around 30° being well suited. This inclination of the handle 12 improves the ergonomics of the holder device.

As a preference, when viewed from the side, as depicted in FIG. 1c, the stick 16 is slightly curved upward. This curvature of the handle 12 further improves the ergonomics of the holder device.

The proximal part 16a is intended to be grasped in the hand by an operator, generally the patient. It preferably exhibits a length, measured along the axis Y from the intersection with the axis Z, greater than 8 cm, preferably greater than 10 cm, preferably greater than 12 cm and/or less than 18 cm, preferably less than 16 cm, preferably less than 14 cm. The width of the proximal part 16a, measured perpendicular to the plane of the axes Y and Z, is preferably greater than 1 cm, preferably greater than 1.5 cm and/or preferably less than 3 cm, a width of 2 cm being well suited.

The length of the distal part 16b, measured along the axis Y from the intersection of the axis Z, is preferably greater than 3 cm, preferably greater than 4 cm and/or preferably less than 8 cm, preferably less than 6 cm, a length of 5 cm being well suited. Its width is preferably identical to that of the proximal part 16a.

Figure 3B:
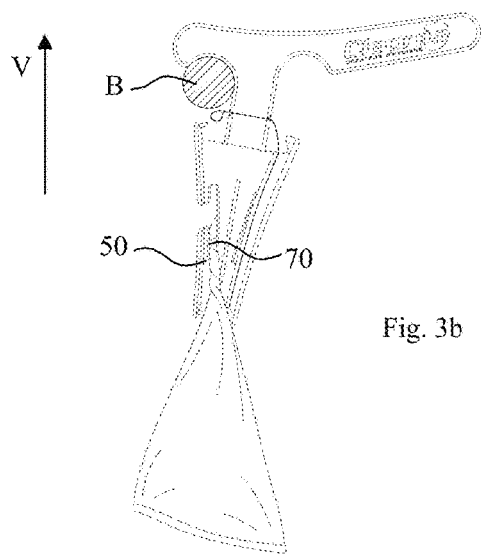
FIGS. 3a and 3b illustrate the packaging of the urinal bag depicted in FIGS. 2a and 2b, respectively.
Figure 3A:
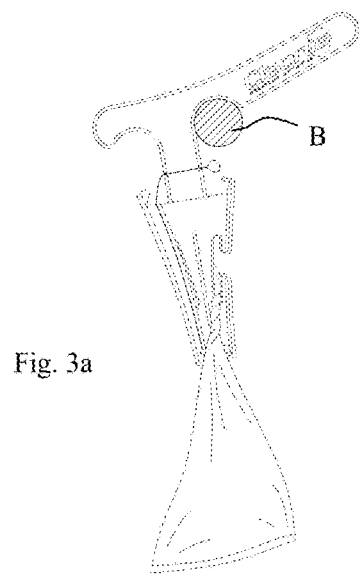

On each side of the crosspiece 18, preferably in the region of the connection of the crosspiece 18 to the stick 16, the handle 12 defines a proximal indentation 22a and a distal indentation 22b which are suited to hanging the holder device from a horizontal bar B, notably a bar of a bed, as depicted in FIGS. 3a and 3b respectively.

As a preference, the proximal and distal indentations are created in the corners formed by the crosspiece 18 on the one hand, and the proximal part 16a and distal part 16b of the stick, respectively. This arrangement improves the stability when hung, but also improves the quality of the grip, as the operator can lodge his or her index finger in the proximal indentation in order the better to control the holder device.

The proximal and distal indentations preferably exhibit a rounded shape, without any sharp edges. As a preference, when viewed from the side, they exhibit the shape of a portion of a circle, preferably substantially the shape of a semicircle, the radius of said portion of a circle preferably being greater than 1 cm and/or less than 2.5 cm, preferably less than 2 cm.

Structurally, the handle 12 comprises, is preferably made up of, a longitudinal web 24, preferably extending vertically and preferably centrally, and of a peripheral flange 26. The peripheral flange 26 preferably extends substantially transversely, namely perpendicular to the longitudinal median plane $P_1$ of the handle 12 and, more preferably still, substantially symmetrically about this plane. The peripheral flange 26 externally surrounds the longitudinal web 24. This mode of construction provides an excellent compromise between the rigidly of the handle and the amount of raw material consumed.

As a preference also, the exterior surface 29 of the peripheral flange 26 extends between the proximal end 27a and the distal end 27b of the stick 26 without defining any reliefs. The exterior surface 29 is therefore smooth to the touch and therefore particularly comfortable.

The width of the peripheral flange is preferably substantially constant all around the stick 16. As a preference, it increases along the crosspiece 18, as it approaches the support 14 (FIG. 1a). The widening of the peripheral flange 26 as it nears the support advantageously stiffens the connection between the support 14 and the crosspiece 18, making the holder device easier to use.

The maximum width of the peripheral flange 26 is preferably greater than 2.5 cm, preferably greater than 3 cm and/or less than 5 cm, preferably less than 4 cm.

The minimum width of the peripheral flange 26 is preferably greater than 0.5 cm, preferably greater than 1 cm, preferably greater than 2 cm.

As a preference, the holder device further comprises a slot 30 configured to elastically hold a closure tie for closing a urinal bag fixed to the support. As a preference, the slot 30 narrows progressively from its opening to its bottom and, more preferably still, exhibits a V shape.

Still as a preference, the slot 30 is created in the peripheral flange 26, more preferably still in the part of the peripheral flange 26 that belongs to the crosspiece 18.

Still as a preference, the holder device comprises 2, 3 or 4 slots 30. As a further preference, the slots 30 are arranged symmetrically with respect to the longitudinal median plane $P_1$ and/or symmetrically with respect to the transverse median plane $P_t$ of the support and/or are equidistant from the axis X.

Figure 2A:
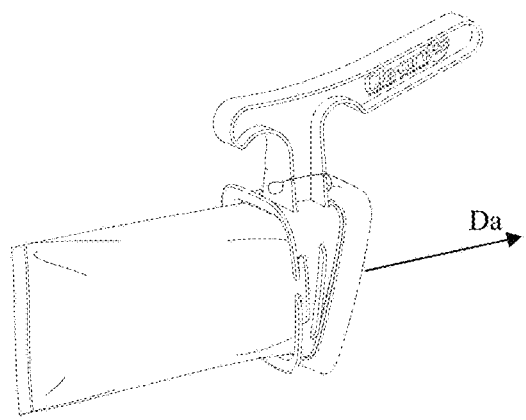

The support 12 comprises proximal 32a and distal 32b spacers designed to hold a urinal bag in open positions referred to as "proximal" and "distal" respectively, as depicted in FIGS. 2a and 2b respectively.

In the proximal and distal open positions, the bag opens in different, proximal Da and distal Db orientations respectively. As a preference, two planes perpendicular to the proximal Da and distal Db orientations respectively make between them an angle less than 20°, than 10°, than 5°, than 1°. As a preference, the proximal and distal orientations are parallel and, more preferably still, colinear, as in the embodiment depicted in the figures.

The structure of the spacer is nonlimiting and any means that allows a urinal bag attached to the support to be held in an open position can be envisioned. In particular, a spacer is not necessarily shaped to bear against the edge of the opening of the bag along the entire length of this edge.

The proximal 32a and distal 32b spacers may be identical or different. As a preference, as in the embodiment depicted, they are identical and, more preferably still, symmetrical with respect to the transverse median plane $P_t$ of the support, which in this instance is vertical and perpendicular to the longitudinal median plane $P_1$.

Only the proximal spacer is therefore described in detail hereinafter.

The proximal spacer 32a comprises a sleeve 36 of axis X of which a proximal edge 37a defines a proximal opening 40a, and a proximal bearing flange 38a extending from said proximal edge, preferably substantially radially outward.

As a preference, the shortest length of the sleeve 36, along the axis X, is greater than 1 cm, preferably greater than 1.5 cm.

The axis of the proximal opening 40a is substantially parallel to the axis of the stick. The stick is, however, spaced radially away from the sleeve, with respect to the axis X, by the crosspiece.

The proximal and distal spacers define proximal and distal openings, respectively, and the crosspiece is configured to space the stick radially away from the axes of these openings, which are preferably substantially parallel to the axis X.

This configuration is particularly practical. Furthermore, it allows the device to be used when the bag is attached to the proximal spacer or to the distal spacer. When the bag is attached to the proximal spacer or to the distal spacer, the stick effectively advantageously allows the proximal bearing flange or the distal bearing flange to be pressed against the skin of the patient, respectively.

The interior surface of the sleeve 36, which is preferably smooth, is preferably cylindrical of axis X and, as a preference, of trapezoidal transverse section. The trapezoidal section thus exhibits in succession a wide base $36_1$, a righthand side $36_2$, a small base $36_3$ and a left-hand side $36_4$. The large base $36_1$ is preferably substantially horizontal. As a preference, it exhibits a length greater than 5 cm, preferably greater than 6 cm and/or less than 8 cm, preferably less than 7 cm. The length of the right hand and left hand sides is preferably greater than 8 cm, preferably greater than 8.5 cm and/or less than 10 cm. Finally, the length of the short base is preferably greater than 2 cm, preferably greater than 2.5 cm and/or less than 4 cm, preferably less than 3.5 cm. Of course, these dimensions are nonlimiting and need to be adapted to suit the urinal bag used.

As a preference, the large base $36_1$ extends substantially horizontally, above the small base. The trapezoidal section therefore points downward.

A trapezoidal section has proven to be particularly ergonomic and well suited to patients of very different builds.

The proximal bearing flange 38a preferably exhibits the form of a blade which extends from the proximal edge of the sleeve substantially perpendicular to the exterior surface of the sleeve 36. The proximal bearing flange 38a exhibits an exterior surface, or "bearing surface" 38e, and an interior surface 38i, opposite to the exterior surface 38e and preferably substantially parallel to the exterior surface 38e (FIG. 1e).

The bearing surface 38e is preferably substantially flat and preferably exhibits a width $l_{38}$, preferably constant, greater than 0.5 cm, preferably greater than 0.8 cm and/or less than 2 cm, preferably less than 1.5 cm, a width of 1 cm being well suited. Such a bearing surface considerably improves the comfort when using the holder device. A substantially flat bearing flange has the function of ensuring a contact surface that limits the extent to which the device digs into the skin. It may notably have a rectilinear or slightly curved profile, the radius of curvature preferably being greater than 1 cm, preferably greater than 2 cm, preferably greater than 3 cm, preferably greater than 5 cm.

The proximal bearing flange 38a preferably forms an angle θ with the exterior surface of the sleeve 36. As a preference, this angle is greater than or equal to 90°, preferably greater than 95°, preferably greater than 100°, preferably greater than 110° and/or preferably less than 140°, preferably less than 130°.

In one preferred embodiment, this angle varies along the proximal bearing flange. As a preference, it is at a maximum along that part of the proximal edge of the sleeve that defines the large base of the transverse section, and at a minimum along that part of the proximal edge of the sleeve that defines the small base of the transverse section. As a preference, even when it varies, the angle θ always remains greater than 90°, preferably greater than 95° and less than 120°.

As an alternative, the angle θ may, however, be substantially constant.

As a preference, the proximal spacer 32a is configured in such a way that the plane $P_a$ of the proximal opening 40a forms, with the transverse median plane $P_t$ of the support, an angle α greater than 10°, preferably greater than 15° and/or less than 30°, preferably less than 25°, preferably of around 20°.

As a preference, the proximal bearing flange 38a is locally uninterrupted by at least one interruption zone 46, preferably by several interruption zones 46 so that it is in a plurality of segments. As a preference, the holder device comprises at least two interruption zones 46, preferably arranged symmetrically with respect to the longitudinal median plane $P_1$ and, more preferably still, substantially midway up the height of the sleeve 36. The length of an interruption zone, measured along the proximal bearing flange 38a, is preferably greater than 0.5 cm, preferably greater than 1 cm and/or less than 2.5 cm, preferably less than 2 cm, a length of around 1.5 cm being well suited.

The interruption of the proximal bearing flange 38a limits the amount of stiffening of the sleeve conferred by the proximal bearing flange 38a, and this makes it easier to fit a urinal bag in the open position.

As a preference, at least one interruption zone 46 extends, in the sleeve 36, in the form of a notch 48. In the preferred embodiment depicted, the device comprises, along the proximal bearing flange 38a, two interruption zones 46 which each extend in the form of a notch 48.

The notches 48 may have the same shape or different shapes.

Each notch 48 contributes to making the sleeve 36 more flexible, making a urinal bag easier to fit.

As a further preference, the shape of a notch 48 is determined so that a bag can be attached thereto by lateral insertion into the notch.

As a preference, the notch 48 exhibits a hook 50, preferably open upward, namely toward the handle, allowing the attachment of a urinal bag, as it is described hereinafter. The dimensions of the hook are determined so that the upper part of the urinal bag can be pinched together after this upper part has been twisted on itself, as depicted in FIG. 3. In other words, the upper part of the urinal bag can be introduced laterally and forcibly into the opening of the hook, then held in the hook by elastic compression. In the embodiment depicted, the hook 50 has a width $l_{50}$ greater than 2 mm, preferably greater than 3 mm and/or preferably less than 8 mm, preferably less than 6 mm, preferably less than 5 mm, a width of 4 mm being well suited. As a preference, the width of the hook 50 is substantially constant. The hook 50 may in particular extend over a height greater than 1 cm, preferably greater than 1.5 m.

On the opposite side to the hook 50, with respect to the interruption zone 46, the notch 48 may also extend.

The proximal spacer also comprises proximal attaching lugs 52a, preferably pointed, for example of triangular shape. The proximal attachment lugs 52a preferably project from the interior surface 38i of the proximal bearing flange 38a. They advantageously improve the attachment of the urinal bag to the proximal spacer. The height of a proximal attachment lug 52a, measured from the interior surface 38i of the proximal bearing flange 38a, is preferably greater than 1 mm, 2 mm, 3 mm, 4 mm and/or less than 8 mm, 7 mm or 6 mm, a height of 5 mm being well suited.

The number of proximal attachment lugs 52a is nonlimiting. In particular, it may be greater than 1 and/or less than 3. In the preferred embodiment depicted, the proximal spacer comprises two proximal attachment lugs 52a projecting from the interior surface 38i and aligned in the longitudinal mid plane $P_1$.

The distal spacer is similar to the proximal spacer and shares the sleeve 36 therewith.

Because of the inclination of the plane $P_a$ of the proximal opening 40a with respect to the transverse median plane $P_t$ of the support, the sleeve 36, when viewed from the side (FIG. 1d) exhibits a trapezoidal shape, the large and short bases of the trapezoid being substantially horizontal and the large base being above the small base. The large base preferably exhibits a length greater than 4 cm, preferably greater than 4.5 cm and/or less than 6 cm, preferably less than 5.5 cm, a length of 5 cm being well suited. The short base preferably exhibits a length greater than 2 cm and/or less than 3 cm, preferably less than 2.5 cm.

Such a shape is particularly ergonomic.

As a preference, at least one transverse rib 56, preferably vertical, extends over the exterior surface of the sleeve 36, preferably in the transverse median plane $P_t$ of the support. In the embodiment depicted, the holder device comprises two ribs 56 arranged symmetrically with respect to the transverse median plane of the support and each extending along a notch 48. The shape and dimensions of the ribs 56 are adjusted according to the desired stiffness of the support.

Furthermore, the ribs 56 act as end stops for the urinal bag after it has been fitted to the proximal spacer, and therefore contribute to the stability of fixing of the urinal bag.

The urinal bag 60 is conventionally a polyethylene bag, preferably opaque, of which the edge of the opening 62 defines an opening 64 in the service position, in which the urinal bag 60 is fixed to a spacer in the open position.

As a preference, the edge of the opening 62 defines a casing through which a closure tie 66, conventionally a string, is introduced, the casing being locally interrupted so that the closure tie 66 can be grasped by the operator.

Finally, the bag 60 preferably contains absorbent padding, not depicted.

For improved ergonomics, the urinal bag 60 preferably has a length greater than 30 cm, preferably greater than 35 cm, and a width, when laid out flat, greater than 14 cm and/or less than 18 cm. As a preference, the length of the bag is greater than twice its width laid out flat.

Operation

The operation of the holder device is directly evident from the foregoing.

Figure 5:
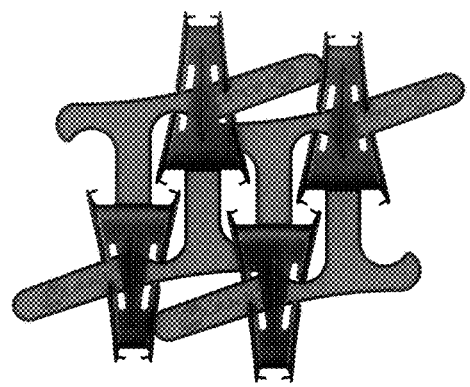
FIG. 5 illustrates one way of storing holder devices according to the invention.
Figure 4A:
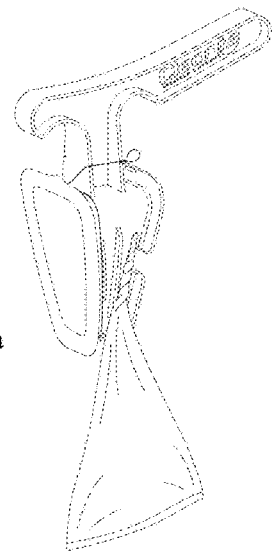

Initially, the holder devices according to the invention may be stored compactly, as depicted in FIG. 5. In particular, a sleeve 36 of one holder device may accept the proximal part of the stick of a second holder device and the distal part of the stick of a third holder device. The shape of the holder device advantageously allows for particularly efficient storage.

To render the holder device operational, an operator introduces a urinal bag 60, via its lower part, through the sleeve 36. In the example considered, it is considered that the urinal bag 60 is introduced via the distal opening (FIG. 2b). The operator then turns the open edge 62 of this bag over around the proximal bearing flange 38a. This operation causes the bag to open and become immobilized on the proximal bearing flange 38a. In particular, the elasticity of the bag, and also the elasticity of the support, make this operation easier, then ensure separation and elastic retention of the bag in its open position, as depicted in FIG. 2b. This retention is further improved by the action of the proximal attaching lugs 52a, which prevent any slippage of the bag that might tend to cause it to come free of the support.

The closure tie 66 is then forcibly inserted into one of the slots 30, which stops it from entering the opening of the bag.

By manipulating the holder device via the handle, the operator can then position the bag in such a way that the patient can urinate into the bag. In particular, the operator may arrange the holder device in such a way that the proximal bearing flange is in contact with the patient's skin. The wide width of the proximal bearing flange limits any risk of injury and makes the holder device particularly comfortable.

If he or she prefers, the operator may alternatively attach the bag to the distal bearing flange 38b, by folding the open edge 62 of this bag around this bearing flange. He or she may then position the holder device in such a way that the distal bearing flange is in contact with the patient's skin. The position of the handle with respect to the patient's skin differs according to whether it is the proximal bearing flange or the distal bearing flange that is in contact with the skin. The device according to the invention thus advantageously offers several possible configurations of use.

The padding progressively absorbs the urine.

The operator then closes the bag by twisting it, for example over three turns, so as to isolate the contents of the bags from the exterior environment. This way of isolating the contents of the bag is advantageously very simple and provides perfect sealing. It renders the closure tie optional.

Without detaching the bag from the proximal spacer, the operator introduces the twisted part 70 of the bag into one of the hooks 50 of the distal spacer, as depicted in FIG. 3b. Advantageously, the hook keeps the bag in the twisted position (FIG. 3b).

The operator can then hang the urinal device consisting of the bag and the holder device, for example on a bar B, preferably exhibiting a diameter of between 1 and 3 cm, as depicted in FIG. 3b. The urinal device can be hung by resting the proximal indentation or the distal indentation against the bar.

As a preference, it is hung from the bar via the distal indentation (FIG. 3b), as that improves stability. As a preference, when the urinal device is in this suspended position hanging on the bar B from the distal indentation, the distal indentation extends substantially vertically above the hook 50 of the support in which the used urinal bag is constricted, as depicted in FIG. 3b.

The urinal device can also be suspended from these two indentations bearing against respective bars.

The urinal device may be collected at any moment by an operator, which may be a different operator than the one that has fixed the bag on the support. The bag can then be detached from the holder device. To do that, the operator pulls on the bag in order to cause the open edge 62 of the bag to come back toward the inside of the sleeve, then extracts it from the sleeve 36.

If appropriate, the caregiver holds the bag away from the proximal attaching lugs 52a to prevent them from opposing this detachment.

The bag can then be closed by means of the closure tie 66. To do that, the operator pulls on this tie while holding onto the bag, and this causes the open edge of the bag to tighten until the bag is closed. The bag can finally be disposed of.

As is now clearly evident, the invention provides a simple, effective, practical, and environmentally sound solution.

Furthermore, the operator can choose the relative arrangement of the bag with respect to the handle, by deciding to fix this bag to the proximal spacer, as described hereinabove, or to the distal spacer (FIG. 2a). The holder device is therefore particularly multifunctional.

Of course, the invention is not restricted to the embodiment described and depicted, which is given for illustrative purposes only.

In particular, other means for holding the bag in the open position are possible. For example, the bag could be kept in the open position by a plurality of attaching lugs or of hooks.

The particularly ergonomic form of the sleeve, of the bearing flange and of the handle is not limiting either.

The invention claimed is:

1. A urinal device comprising:
a urinal bag and
a holder device comprising a urinal bag support and a handle fixed to the support,
wherein the support comprises first and second spacers configured to keep the urinal bag in first and second open positions respectively, in which first and second open positions the bag opens in first and second different orientations respectively, each of the first and second spacers defining a bearing flange configured so that, in service, it bears against the skin of a patient, said bearing flange having a width greater than 0.5 cm.

2. The urinal device as claimed in claim 1, wherein each bearing flange has a width greater than 0.8 cm.

3. The urinal device as claimed in claim 1, wherein each bearing flange is substantially flat.

4. The urinal device as claimed in claim 1, wherein each bearing flange is interrupted by at least one interruption zone.

5. The urinal device as claimed in claim 1, wherein the first and second orientations are opposite directions.

6. The urinal device as claimed in claim 1, wherein the holder device comprises a hook designed to allow said bag to be constricted while said bag is fixed to any one of the first and second spacers, so as to isolate an interior volume of said bag from the exterior environment.

7. The urinal device as claimed in claim 1, wherein the holder device comprises a slot for affixing, by forceable insertion, a closure tie for closing said bag.

8. The urinal device as claimed in claim 1, wherein at least one bearing flange defines an opening which extends in an overall plane that forms, with a transverse median plane of the support, an angle greater than 10° and less than 30°.

9. The urinal device as claimed in claim 1, wherein the holder device comprises an attaching lug projecting from at least one bearing flange over a height greater than 1 mm and less than 8 mm.

10. The urinal device as claimed in claim 1, wherein the support comprises a sleeve provided, at each of its two ends, with one said bearing flange.

11. The urinal device as claimed in claim 10, wherein the sleeve is cylindrical with a trapezoidal transverse section, the trapezoidal transverse section pointing in the opposite direction to the handle.

12. The urinal device as claimed in claim 1, wherein the handle comprises a stick and a crosspiece rigidly connecting the handle to the support, the crosspiece being designed to space the stick radially away from the axes of the first and second openings which are defined by the first and second spacers, respectively, the minimum distance between the stick and the support being greater than 2 cm.

13. The urinal device as claimed in claim 1, wherein the handle defines at least one indentation configured to allow the holder device to be hung stably from a horizontal bar exhibiting a diameter greater than 1 cm.

14. The urinal device as claimed in claim 13, wherein the handle comprises a stick made up of a proximal part and a distal part, and a crosspiece rigidly connecting the stick to the support and connected to the juncture between the proximal and distal parts of the stick, said indentations being created in the corners formed by the crosspiece on the one hand, and by the proximal and distal parts of the stick, respectively.

15. The urinal device as claimed in claim 14, wherein the stick extends in an overall direction that forms, with a plane perpendicular to the crosspiece, an angle greater than 10°.

16. The urinal device as claimed in claim 1, wherein the handle is formed integrally with the support.

17. The urinal device as claimed in claim 1, wherein the handle is made up of a web edged with a peripheral flange exhibiting a minimum width greater than 0.5 cm.

18. The urinal device as claimed in claim 1, wherein the bearing flanges of the first and second spacers are configured to hold the urinal bag elastically in the first and second open positions, respectively.

19. A method for packaging a urinal bag initially fixed removably to a spacer of a holder device and held in the open position by said spacer, said method comprising a step wherein the bag is constricted in a notch of the holder device so as to isolate an interior volume of the bag from the exterior environment, in which method the bag and the holder device form a urinal device as claimed in claim 1.

20. The method as claimed in claim 19, wherein, as the urinal bag is inserted into the notch it remains held in the open position by said spacer.

21. The method as claimed in claim 19, wherein prior to being inserted in the notch, the part of the bag that is to be inserted into the notch is twisted on itself by more than one turn.

22. The method as claimed in claim 19, wherein, after the being inserted in the notch, the holder device is hung from a bar of a bed.

* * * * *